United States Patent [19]

Ryan

[11] Plant 4,746

[45] Jun. 23, 1981

[54] IMPATIENS PLANT

[76] Inventor: John J. Ryan, 39877 Sundale Dr., Fremont, Calif. 94538

[21] Appl. No.: 150,301

[22] Filed: May 16, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—James R. Cypher

[57] ABSTRACT

This invention relates to a new and distinct variety of New Guinea Impatiens plant, known by the cultivar name Mohegan, a seedling resulting from the cross pollenation of unpatented pollen parent 76-49-1 and unpatented pistil parent 76-45-1 and is distinguished by its very dark, red-purple flower; upright growth habit; desirable response to age and feeding by producing larger flowers (5.0 cm to 6.5 cm in length and width), and distinctive dark reddish-green, dark chocolate brown looking foliage characterized by darker red spots upon close observation.

3 Drawing Figures

BACKGROUND OF THE INVENTION

The present new variety (seedling) was discovered by me in a commercial greenhouse in Fremont, Calif., as a result of a definite breeding program to produce improved and different commercial varieties of plants.

The cross pollenation of unpatented pistil parent 76-45-1 and unpatented pollen parent 76-49-1, produced the distinct new variety herein described and selected for propagation by cuttings. Repeating propagations and flowerings of my new variety through asexual reproduction by terminal or stem cuttings grown in pots in a plastic (polyethylene) greenhouse in Fremont, Calif., under normal environmental conditions show that the characteristics described come true to form and are established and transmitted through succeeding generations.

BRIEF SUMMARY

The known commercial variety to which Mohegan would be closest in characteristics is a seedling that I invented, known by the cultivar name Chinook, for which a U.S. plant patent application was executed on May 14, 1980.

Mohegan has the following characteristics:

1. Mohegan is similar in flower color to Chinook, but Mohegan is a darker shade of red-purple and the flower color could be described as a deep fuchsia,
2. Chinook has a spreading growth habit, whereas the growth habit of Mohegan is upright,
3. Mohegan has larger blossoms than Chinook. The flower is 5.0 cm to 6.5 cm. in length and width,
4. Mohegan does not produce as many blossoms as Chinook,
5. The color of the foliage of Mohegan is dark reddish-green and could be described as dark chocolate brown, but Chinook has an even darker reddish-green foliage appearing almost metallic (black-green with a dull shine),
6. Close observations of the foliage of Mohegan reveals that the red pigment (reddish overcoating) is not consistently distributed but appears flecked or blotched with darker red spots,
7. Mohegan seems to display its own particular response to maturation and feeding in that the mature, well fed plant produces much larger flowers than those first appearing on the plant. This is a response that is much more traumatic than I have observed in other impatiens plants.

DESCRIPTION OF PHOTOGRAPH

Photograph No. 1 illustrates the overall appearance and form of the plant as well as the nature and color of its flowers and foliage, the color rendition being as nearly true as is reasonably possible to obtain by conventional photographic procedures. The photograph was taken under intensive light conditions.

Photograph No. 2 is a close up of three blossoms attached to a small branch of the plant and three blossoms unattached. This photo illustrates the red-purple (described as deep fuchsia) color of the flowers.

Photograph No. 3 is a close up of the leaves of the plant and illustrates the dark reddish-green (described as dark chocolate brown) color of the foliage.

DETAILED DESCRIPTION

Referring to the botanical details of my new variety, the following detailed description is based on observations made on Mar. 10, 1980. All plants were grown under normal environmental conditions in greenhouses. Color readings were taken during daylight hours in full sun, and all colors are based on the Royal Horticultural Society Colour Chart.

PLANT

Name: Mohegan.

Origin: Seedling of the cross-pollenation of the unpatented pistil parent 76-45-1 and the unpatented pollen parent 76-49-1.

Form: Upright to slightly spreading.

Height to flowering: 38 cm to 46 cm.

Growth: Fast.

Type of cutting: Terminal or stem.

Rooting time: Typical, 10–14 days.

Rooting habit: Fast, dendritic.

FOLIAGE

Arrangement: Lower leaves of any break opposite (usually one set); upper foliage of any break whorls of 3 to 9 (seem to be two compressed nodes, however, 9 is usually 3 of 3 leaves).

Shape: A few young leaves oblanceolate. Many older leaves lanceolate to elliptical and asymmetric.
Tip: Acuminate.
Base: Attenuate.
Margin: Serrulate.
Veination: Pinnate.
Size: Length of blade and petiole 9.0 cm to 15.0 cm; length of blade 7.0 cm to 12.5 cm; width of blade at widest point 2.5 cm to 4.0 cm.
Surface: Glabrous.
Variegation: None.
Color:
1. *Petiole.*—185A.
2. *Veins.*—185A.
3. *Leaf.*—a. Upper 137A darkened by read overlay-with flecks of 187A. b. Lower 184A on young leaf with flecks (splotches) of 184B.

STEM

Color: 185B.
Internode:
1. *Length.*—Moderate.
2. *Size.*—Moderate.

Node expanded (relative to internode): definitely expanded.
Breaking action: Average.

FLOWER

Form: Typical.
Borne: End of branches, terminal.
Blooming habit:
1. *Relative number.*—Average.
2. *Time to flowering.*—Longer than average.
3. *Longevity.*—3 to 5 days.

Size of mature flower: First flower on a plant is small; flowers get much larger with age and abundant food.
1. *Length.*—5.0 cm to 6.5 cm.
2. *Width.*—5.0 cm to 6.5 cm.
3. *Spur.*—6.5 cm to 7.0 cm.

Color: Lightens under high light.
1. *Eye.*—46A.
2. *Middle.*—66A.
3. *Edge.*—66A.
4. *Pedicel.*—146B to 146C.

REPRODUCTIVE ORGANS

Stamen:
1. *Anthers.*—Typical, fused hood (53B) over pistil.
2. *Filaments.*—Typical, fused hood (53B) over pistil.
3. *Pollen.*—a. Color 158C. b. Abundance—plenty.

Pistils:
1. *Style.*—Typical, end of style 187A.
2. *Ovaries.*—Typical, end of style 187A.

OTHER CHARACTERISTICS

Mohegan seems to display its own particular response to age and feeding in that a mature well fed plant bears large flowers whereas the first flowers are usually small. Mohegan also can show flower distortion both in color and form especially on first flowers of a shoot.

I claim:

1. A new and distinct form of Impatiens plant as described and illustrated, known by the cultivar name Mohegan.

* * * * *

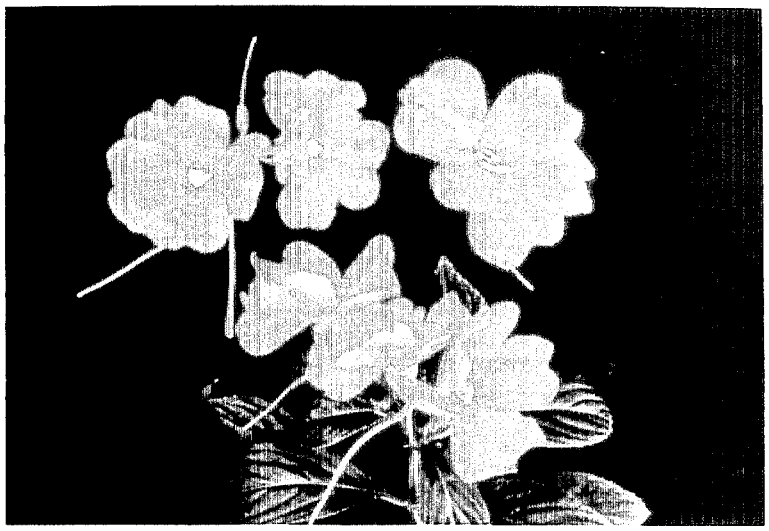
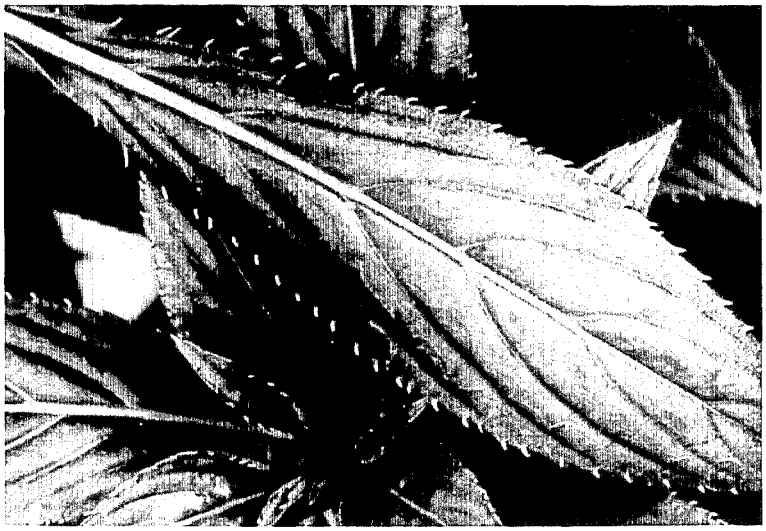

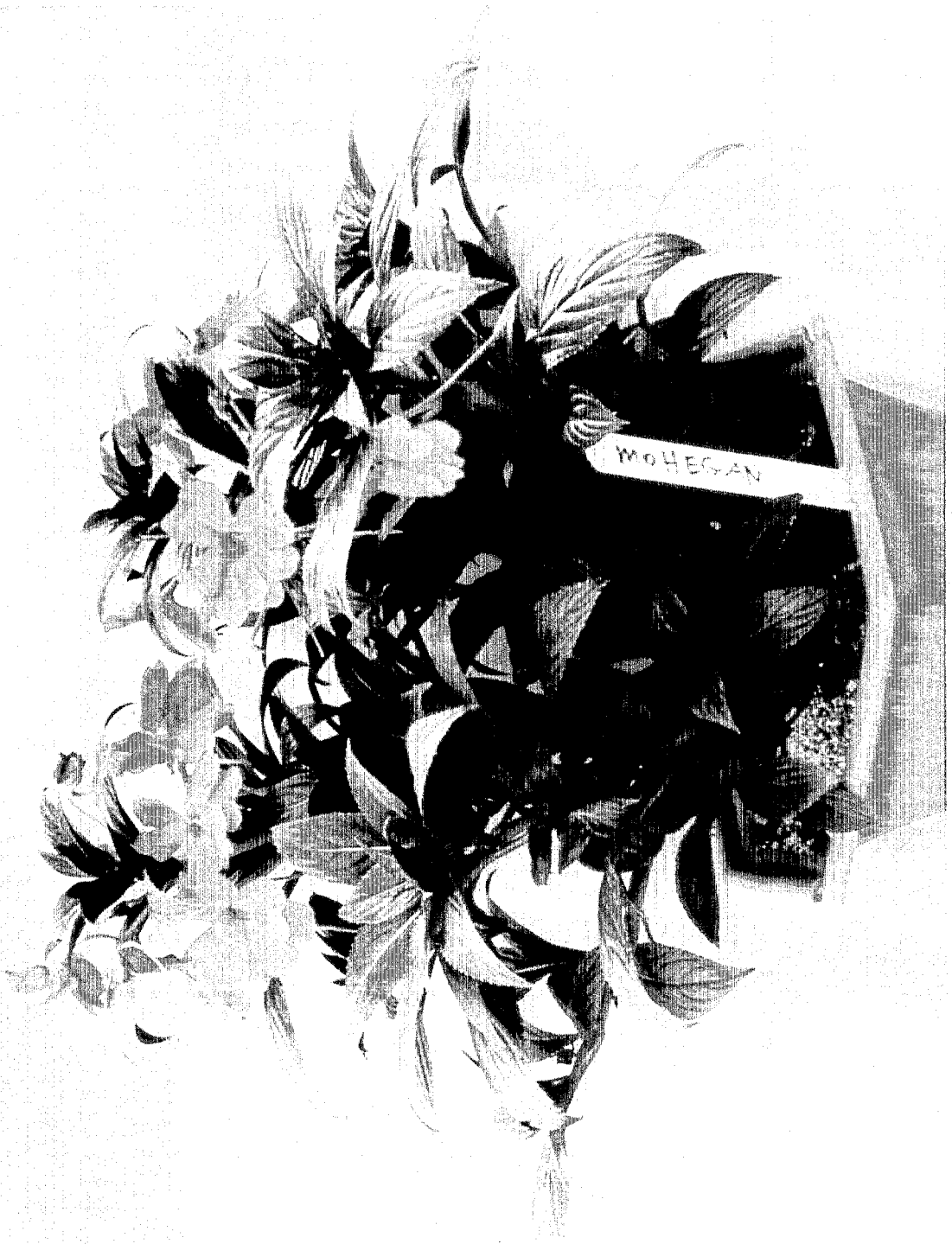
MOHEGAN